US005922573A

United States Patent [19]

Boraschi et al.

[11] Patent Number: 5,922,573

[45] Date of Patent: Jul. 13, 1999

[54] IL-1 RECEPTOR ANTAGONISTS WITH ENHANCED INHIBITORY ACTIVITY

[75] Inventors: Diana Boraschi; Paola Bossu´; Paolo Ruggiero; Giovanni Macchia; Aldo Tagliabue; Francesco Frigerio, all of Milan; Renata Grifantini, Camerino; Gianni Frascotti; Guido Grandi, both of Milan, all of Italy

[73] Assignee: Dompe' S.p.A., L'Aquila, Italy

[21] Appl. No.: 08/809,185

[22] PCT Filed: Sep. 20, 1995

[86] PCT No.: PCT/EP95/03708

§ 371 Date: Apr. 15, 1997

§ 102(e) Date: Apr. 15, 1997

[87] PCT Pub. No.: WO96/09323

PCT Pub. Date: Mar. 28, 1996

[30] Foreign Application Priority Data

Sep. 21, 1994 [IT] Italy .............................. M194A01916

[51] Int. Cl.[6] ............................ C12N 15/19; C07K 14/54

[52] U.S. Cl. .................. 435/69.52; 435/69.5; 435/252.3; 435/320.1; 435/7.1; 435/7.2; 536/23.5; 530/351; 424/85.1; 424/85.2; 514/2; 930/141

[58] Field of Search .......................... 536/23.5; 435/69.5, 435/69.52, 252.3, 320.1, 7.1, 7.2; 530/351; 424/85.1, 85.2; 514/2; 930/141

[56] References Cited

FOREIGN PATENT DOCUMENTS 9117184 11/1991 WIPO .
92/16221 10/1992 WIPO .

OTHER PUBLICATIONS

Proceedings of the National Academy of Sciences of USA, vol. 88, Apr. 1991, pp. 2658–2662, "Conversion of the Interleukin 1 Receptor Antagonist into an Agonist by Site Specific Mutagenesis", G. Ju et al.

International Journal of Immunopathology and Pharmacology, vol. 7, No. 3, pp. 235–239, Sep.–Dec. 1994, "Pharmacological Exploitation of IL–1 and IL–1 Related Molecules", A. Tagliabue et al.

Journal of Biological Chemistry, vol. 270, No. 19, pp. 11477–11483, "Mapping Receptor Binding Sites in Interleukin (IL)–1 Receptor Antagonist and IL–1 β By Site–Directed Mutagenesis", R.J. Evans et al.

Greenfeder et al IBC 270(38) 1995, pp. 22460–22466.

Baraschi et al *J. Immunol* 1955, 155, 4719–25.

Simoncsits et al *Cytokine* 6(2) 1994, 206–14.

Cloney et al, *Acta Cry. Sect. D. Biol Crys* 50(2) 1994, pp. 197–201 (abstract only).

Lebedenso et al *Biosy Khim* 1993, 19(5) 586–88 (abst. only).

Maurizi et al, *Protein Expression & Purification,* vol 9 1997, pp. 219–227

Chang et al, *Immunological Invest* 25(4) 1996, pp. 355–368.

Wieczorek et al *Polish J. Pharmacology* 49, 1997, pp. 107–117.

Ngo et al, Chapter 14, The Protein Folding Problem and Querdary Structure Prediction, ed Merz et al, 1994. p. 433.

Bowie et al, *Science* 247, 1990, p. 1306.

Frömmel et al, *J. Mol. Eval* 21, 1985, pp. 233–257.

*Primary Examiner*—Garnette D. Draper
*Attorney, Agent, or Firm*—Griffin, Butler, Whisenhunt & Szipl

[57] ABSTRACT

DNA molecules that code for IL-1 antagonists with improved biological activity arc described. DNA molecules coding for improved IL-1 antagonists inserted into expression vectors and host cells transformed with the said vectors containing the DNA coding for improved IL-1 antagonists and a method for the production of improved IL-1 antagonists in essentially pure form are also described. Preparations that can be injected or can be administered by some other route, consisting of a pharmaceutical preparation of the said mutants, are particularly useful as drugs in the field of therapy.

17 Claims, 2 Drawing Sheets

MAP OF THE EXPRESSION PLASMID pRSETA-IL1ra

SEQUENCE LISTING

```
(1) GENERAL INFORMATION:

   (iii) NUMBER OF SEQUENCES: 8


(2) INFORMATION FOR SEQ ID NO: 1:

     (i) SEQUENCE CHARACTERISTICS:
          (A) LENGTH: 531 base pairs
          (B) TYPE: nucleic acid
          (C) STRANDEDNESS: both
          (D) TOPOLOGY: both

    (ii) MOLECULE TYPE: cDNA

   (iii) HYPOTHETICAL: NO

   (iii) ANTI-SENSE: NO

    (vi) ORIGINAL SOURCE:
          (A) ORGANISM: Homo sapiens

    (ix) FEATURE:
          (A) NAME/KEY: CDS
          (B) LOCATION: 1..531

    (ix) FEATURE:
          (A) NAME/KEY: sig_peptide
          (B) LOCATION: 1..75

    (ix) FEATURE:
          (A) NAME/KEY: mat_peptide
          (B) LOCATION: 76..531

    (ix) FEATURE:
          (A) NAME/KEY: mutation
          (B) LOCATION: replace(346..348, "cgc")
          (D) OTHER INFORMATION: /note= "CGC is the codon for the preferred
           Asn -> Arg amino acid substitution at this
           position."

    (ix) FEATURE:
          (A) NAME/KEY: mutation
          (B) LOCATION: replace(400..402, "gcc")
          (D) OTHER INFORMATION: /note= "GCC is the codon for the
          preferred Thr -> Ala amino acid substitution at this
           position."
```

(xi) SEQUENCE DESCRIPTION: SEQ ID NO: 1:

```
ATG GAA ATC TGC AGA GGC CTC CGC AGT CAC CTA ATC ACT CTC CTC CTC        48
Met Glu Ile Cys Arg Gly Leu Arg Ser His Leu Ile Thr Leu Leu Leu
-25                 -20                 -15                 -10

TTC CTG TTC CAT TCA GAG ACG ATC TGC CGA CCC TCT GGG AGA AAA TCC        96
Phe Leu Phe His Ser Glu Thr Ile Cys Arg Pro Ser Gly Arg Lys Ser
                 -5                   1               5

AGC AAG ATG CAA GCC TTC AGA ATC TGG GAT GTT AAC CAG AAG ACC TTC       144
Ser Lys Met Gln Ala Phe Arg Ile Trp Asp Val Asn Gln Lys Thr Phe
         10                  15                  20

TAT CTG AGG AAC AAC CAA CTA GTT GCT GGA TAC TTG CAA GGA CCA AAT       192
Tyr Leu Arg Asn Asn Gln Leu Val Ala Gly Tyr Leu Gln Gly Pro Asn
     25                  30                  35

GTC AAT TTA GAA GAA AAG ATA GAT GTG GTA CCC ATT GAG CCT CAT GCT       240
Val Asn Leu Glu Glu Lys Ile Asp Val Val Pro Ile Glu Pro His Ala
 40                  45                  50                  55

CTG TTC TTG GGA ATC CAT GGA GGG AAG ATG TGC CTG TCC TGT GTC AAG       288
Leu Phe Leu Gly Ile His Gly Gly Lys Met Cys Leu Ser Cys Val Lys
                 60                  65                  70

TCT GGT GAT GAG ACC AGA CTC CAG CTG GAG GCA GTT AAC ATC ACT GAC       336
Ser Gly Asp Glu Thr Arg Leu Gln Leu Glu Ala Val Asn Ile Thr Asp
             75                  80                  85

CTG AGC GAG AAC AGA AAG CAG GAC AAG CGC TTC GCC TTC ATC CGC TCA       384
Leu Ser Glu Asn Arg Lys Gln Asp Lys Arg Phe Ala Phe Ile Arg Ser
         90                  95                 100

GAC AGT GGC CCC ACC ACC AGT TTT GAG TCT GCC GCC TGC CCC GGT TGG       432
Asp Ser Gly Pro Thr Thr Ser Phe Glu Ser Ala Ala Cys Pro Gly Trp
    105                 110                 115

TTC CTC TGC ACA GCG ATG GAA GCT GAC CAG CCC GTC AGC CTC ACC AAT       480
Phe Leu Cys Thr Ala Met Glu Ala Asp Gln Pro Val Ser Leu Thr Asn
120                 125                 130                 135

ATG CCT GAC GAA GGC GTC ATG GTC ACC AAA TTC TAC TTC CAG GAG GAC       528
Met Pro Asp Glu Gly Val Met Val Thr Lys Phe Tyr Phe Gln Glu Asp
                140                 145                 150

GAG                                                                   531
Glu
```

(2) INFORMATION FOR SEQ ID NO: 2:

(i) SEQUENCE CHARACTERISTICS:
(A) LENGTH: 177 amino acids
(B) TYPE: amino acid
(D) TOPOLOGY: linear (ii) MOLECULE TYPE: protein (xi) SEQUENCE DESCRIPTION: SEQ ID NO: 2:

```
Met Glu Ile Cys Arg Gly Leu Arg Ser His Leu Ile Thr Leu Leu Leu
-25                 -20                 -15                 -10

Phe Leu Phe His Ser Glu Thr Ile Cys Arg Pro Ser Gly Arg Lys Ser
                 -5                   1               5

Ser Lys Met Gln Ala Phe Arg Ile Trp Asp Val Asn Gln Lys Thr Phe
         10                  15                  20

Tyr Leu Arg Asn Asn Gln Leu Val Ala Gly Tyr Leu Gln Gly Pro Asn
     25                  30                  35

Val Asn Leu Glu Glu Lys Ile Asp Val Val Pro Ile Glu Pro His Ala
 40                  45                  50                  55

Leu Phe Leu Gly Ile His Gly Gly Lys Met Cys Leu Ser Cys Val Lys
                 60                  65                  70
```

```
Ser Gly Asp Glu Thr Arg Leu Gln Leu Glu Ala Val Asn Ile Thr Asp
             75                  80                  85

Leu Ser Glu Asn Arg Lys Gln Asp Lys Arg Phe Ala Phe Ile Arg Ser
        90                  95                 100

Asp Ser Gly Pro Thr Thr Ser Phe Glu Ser Ala Ala Cys Pro Gly Trp
    105                 110                 115

Phe Leu Cys Thr Ala Met Glu Ala Asp Gln Pro Val Ser Leu Thr Asn
120                 125                 130                 135

Met Pro Asp Glu Gly Val Met Val Thr Lys Phe Tyr Phe Gln Glu Asp
                140                 145                 150

Glu
```

(2) INFORMATION FOR SEQ ID NO: 3:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: cDNA (iii) HYPOTHETICAL: NO (iii) ANTI-SENSE: NO (v) FRAGMENT TYPE: N-terminal (vi) ORIGINAL SOURCE:
(A) ORGANISM: Homo sapiens (xi) SEQUENCE DESCRIPTION: SEQ ID NO: 3:

GATCATATGC GACCCTCTGG GAGAAAATCC 30

(2) INFORMATION FOR SEQ ID NO: 4:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: cDNA (iii) HYPOTHETICAL: NO (iii) ANTI-SENSE: NO (v) FRAGMENT TYPE: C-terminal (vi) ORIGINAL SOURCE:
(A) ORGANISM: Homo sapiens (xi) SEQUENCE DESCRIPTION: SEQ ID NO: 4:

GATCTGCAGC TACTCGTCCT CCTGGAAG 28

(2) INFORMATION FOR SEQ ID NO: 5:

(i) SEQUENCE CHARACTERISTICS:
(A) LENGTH: 34 base pairs
(B) TYPE: nucleic acid
(C) STRANDEDNESS: single
(D) TOPOLOGY: linear (ii) MOLECULE TYPE: cDNA (iii) HYPOTHETICAL: NO (iii) ANTI-SENSE: NO (v) FRAGMENT TYPE: N-terminal (vi) ORIGINAL SOURCE:
(A) ORGANISM: Homo sapiens (xi) SEQUENCE DESCRIPTION: SEQ ID NO: 5:

GGGAATTCTT ATGCGACCCT CTGGGAGAAA ATCC 34

(2) INFORMATION FOR SEQ ID NO: 6:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: cDNA (iii) HYPOTHETICAL: NO (iii) ANTI-SENSE: NO (v) FRAGMENT TYPE: C-terminal (vi) ORIGINAL SOURCE:
(A) ORGANISM: Homo sapiens (xi) SEQUENCE DESCRIPTION: SEQ ID NO: 6:

GGCTGCAGCT ACTCGTCCTC CTGGAAG 27

(2) INFORMATION FOR SEQ ID NO: 7:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (iii) HYPOTHETICAL: NO (iii) ANTI-SENSE: NO (v) FRAGMENT TYPE: internal (vi) ORIGINAL SOURCE:
(A) ORGANISM: Homo sapiens (ix) FEATURE:
(A) NAME/KEY: -
(B) LOCATION: 13..15
(D) OTHER INFORMATION: /note= "anticodon corresponding to amino acid 91 of mature IL-1ra"

(xi) SEQUENCE DESCRIPTION: SEQ ID NO: 7:

GTCCTGCTTT CTGCGCTCGC TCAG 24

(2) INFORMATION FOR SEQ ID NO: 8:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA (iii) HYPOTHETICAL: NO (iii) ANTI-SENSE: NO (v) FRAGMENT TYPE: internal -continued

```
(vi) ORIGINAL SOURCE:
      (A) ORGANISM: Homo sapiens

(ix) FEATURE:
      (A) NAME/KEY: -
      (B) LOCATION: 10..12
      (D) OTHER INFORMATION: /note= "anticodon corresponding to
           amino acid 109 of mature IL-1ra"

(xi) SEQUENCE DESCRIPTION: SEQ ID NO: 8:

CTCAAAACTG GCGGTGGGGC C                                           21
```

IL-1 RECEPTOR ANTAGONISTS WITH ENHANCED INHIBITORY ACTIVITY

The present invention relates to mutants of the IL-1 receptor antagonist (IL-1ra ), with an improved inhibitory activity compared to the wild type antagonist, means and methods for their preparation, and their use in the therapeutic sector in all pathologies in which IL-1 is thought to be involved.

BACKGROUND OF THE INVENTION

IL-1 (interleukin-1) is the cytokine that the body produces, in response to infections, various kinds of attack or antigenic stimulation, to initiate a defence reaction of the inflammatory or immune type. IL-1 is a polypeptide of approx. 17.5 kDa in its mature form, produced mainly by the macrophages but also by epidermal, lymphoid, vascular and epithelial cells. IL-1 is one of the principal stimulating factors of both the inflammatory and immune responses and, in its circulating form, it is capable of acting as a hormone, inducing a broad spectrum of systemic changes at metabolic, neurological, haematological and endocrinological level. Thus, IL-1 exerts an influence on mesenchymal tissue remodelling, contributing both to destructive processes and to repair processes. Furthermore, IL-1 is an activator of lymphocytes and plays a fundamental role in the initiation and amplification of the immune response. IL-1 also possesses strong activity of the inflammatory type, for example stimulation of the production of prostanoids and of proteases in various cells, including chondrocytes, fibroblasts, synovial cells, and brain cells. Thus, IL-1 is involved in many components of the acute-phase response and is the endogenous mediator of fever (endogenous pyrogen). IL-1 can act in synergy with other cytokines, especially TNFα, significantly amplifying its inflammatory activity.

Cloning of IL-1 has led to the identification of two active forms. The predominant form is IL-1β, synthesized as an inactive precursor of 269 amino acids (31 kDa), which is then cut by a protease to give rise to the active mature form (corresponding to amino acids 117–269 of the precursor). A form that occurs about a hundred times less frequently, and is generally associated with the cells, is IL1α, which has about 26% homology with IL1β, and which is also synthesized as a precursor of 271 amino acids (which, however, possesses biological activity), which then gives rise to the mature form after proteolysis of the precursor. IL-1 represents a special case among the cytokines (together with fibroblast growth factor=FGF) in that it lacks a signal peptide and so is not secreted via the normal routes. The most abundant extracellular form therefore consists of the mature form of IL1β, which is thus responsible for the majority of the biological activities of IL-1, both immunostimulant and inflammatory.

In view of such activities, it has been hypothesized that IL-1 might have a role in the pathogenesis of inflammatory and autoimmune diseases. Thus, in the vast majority of pathologies of acute and chronic inflammation and in many autoimmune pathologies, increased production of IL-1β has been identified as one of the main factors responsible for the pathology (Dinarello C.A. Blood 77: 1, 1991).

The biological activities of IL-1 are inhibited in the presence of specific inhibitors. In view of IL-1's fundamental role in the pathogenesis of many autoimmune diseases and of chronic inflammatory diseases with tissue destruction, it is suggested that inhibition of IL-1 could be useful in the treatment of these pathologies. IL-1ra (IL-1 receptor antagonist) is a cytokine that is structurally very similar to IL-1, but is synthesized with a signal peptide and secreted as mature glycosylated protein. A non-glycosylated intracellular form of IL-1ra , with seven extra amino acids and without a signal peptide, with activity comparable to that of secreted IL-1ra , has also been described. IL-1ra is capable of binding effectively to IL-$1R_I$ and much less well to IL-$1R_{II}$. IL-$1R_I$, the type I IL-1 receptor, is a receptor that belongs to the immunoglobulin superfamily, composed of an extracellular domain (which has three immunoglobulin-like units bound by disulphide bridges), a transmembrane sequence that anchors the receptor to the cell, and an intracellular domain that is responsible for transmitting the activation signal to the interior of the cell. The other IL-1 receptor, IL-$1R_{II}$, is structurally very similar to IL-$1R_I$ in the extracellular and transmembrane part, but possesses practically no intracellular domain and therefore does not seem capable of transmitting the activation signal. It is therefore hypothesized that IL-$1R_{II}$ does not have the ability to activate the cells and that IL-$1R_I$ is largely responsible for cell activation in response to IL-1 (Arend W.P. J. Clin. Invest. 88: 1445, 1991; Dinarello C.A. & Thompson R.C. Immunol. Today 11: 404, 1991). IL-$1R_{II}$ is released naturally by the cell membrane, probably through the action of a specific protease, and once it is free in the extracellular space it is able to capture circulating IL-1β and prevent it from interacting with membrane IL-$1R_I$, so that it functions as an IL-1 inhibitor. However, the actual biological role of IL-$1R_{II}$, apart from capture and inhibition of IL-1 when released by the cell in soluble form, has not yet been elucidated definitively and there are data in various systems that suggest possible cell activation that is dependent on IL-$1R_{II}$ (Boraschi et al. Neuro-Immunology of Fever p. 19, 1992; Luheshi G. et al. Am. J. Physiol. 265: E585, 1993; Kent S. et al. Proc. Natl. Acad. Sci. USA 89: 9117, 1992. IL-1ra does not have IL-1-like biological activity, in that it occupies IL-$1R_I$ without activating the cell, and in occupying the receptor it functions as an antagonist of IL-1 activity. On account of its antagonist activity, IL-1ra has been used successfully in experimental models of inflammation induced by IL-1, by LPS (a bacterial endotoxin) and by live bacteria, to inhibit the inflammatory, toxic and lethal pathologic effects of the treatments (Ohlsson K. et al. Nature 348: 550, 1990; Wakabayashi G. et al. FASEB J. 5: 338, 1991; Alexander H.R. et al. J. Exp. Med. 173: 1029, 1991; Fischer E. et al. J. Clin. Invest. 89: 1551, 1992). However, in view of the extreme potency of IL-1 (which can activate cells by occupying fewer than ten receptors/cell), the doses of IL-1ra necessary to obtain significant therapeutic effects in vivo are extremely high. Trials in humans in septic shock have shown a marginal efficacy of IL-1ra even at extremely high doses (Fischer C. J. et al., J.A.M.A. 271: 1836, 1994). Accordingly, it is particularly useful to be able to modify the structure of IL-1ra so as to increase its capacity for interaction with IL-$1R_I$ and so improve its therapeutic efficacy. An IL-1ra mutant having a glycine instead of asparagine in position 91 has been recently disclosed (Evans R. et al. J. Biol. Chem., 11477, 1995).

SUMMARY OF THE INVENTION

The present invention relates to IL-1ra mutants that can be used as drugs in the therapeutic field, to inhibit the pathogenetic activities of IL-1 with increased efficacy. More particularly, the field of the invention comprises:

- mutants of IL-1ra with improved inhibitory activity, characterized in that at least one of the two amino acid residues in positions 91 and 109 of the sequence of wild type (wt) IL-1ra is replaced by a different residue;

DNA sequences coding for the said mutants;

expression vectors comprising the said sequences;

host microorganisms transformed with the said vectors;

methods for the production of these mutants by culturing the transformed host microorganisms in appropriate conditions;

use of the mutants of IL-1ra for inhibiting the biological activities of IL-1;

pharmaceutical compositions comprising a therapeutically effective amount of at least one mutant of IL-1ra , a carrier and/or a pharmacologically acceptable solvent, which can be used for inhibiting the activities of IL-1, especially in situations where IL-1 could be involved in the pathological process.

DETAILED DESCRIPTION OF THE INVENTION

Figure 1:
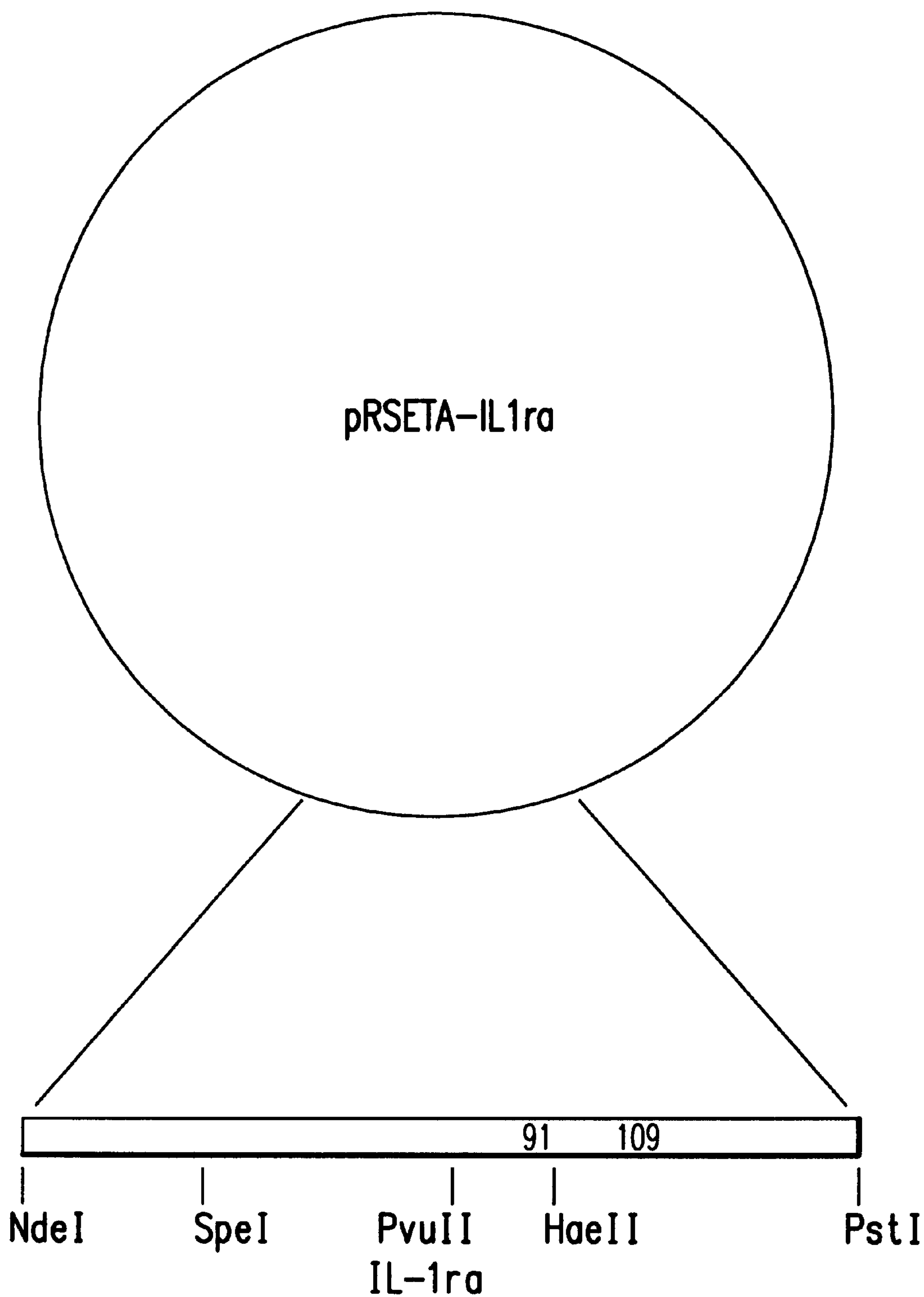
FIG. 1 shows a map of expression plasmid pRSETA-IL1ra.

The present invention relates to IL-1ra mutants and to pharmaceutical preparations containing them, as active principle for the therapeutic use as an IL-1 antagonist to inhibit the activities of IL-1 in vivo. The mutants of the invention have potential uses in the treatment of tumours, inflammatory and autoimmune diseases of the lung and airways, CNS, kidney, joints, endocardium, pericardium, eyes, ears, skin, gastrointestinal tract, urogenital system, in septic shock, bone and cartilage resorption, rheumatoid arthritis, atherosclerosis and other chronic inflammatory pathologies with or without autoimmune involvement.

The mutants of the invention are characterized by the replacement of the amino acid residue in position 91 with an amino acid residue selected from glutamine, arginine, lysine, histidine and tyrosine and/or in position 109 with an amino acid residue selected from serine, alanine, phenylalanine, valine, leucine, isoleucine, methionine. Said mutants are prepared by means of molecular techniques of mutagenesis, to produce polypeptides that contain the sequence of IL-1ra , modified so as to improve its capacity for interacting with IL-1R, and therefore enhance its capacity as IL-1 antagonist. Table 1 shows the nucleotide and amino acid sequence of IL-1ra (Sequence ID No. 1 and 2, respectively). Table 2 shows the amino acid sequence of IL-1ra with indication of the selected mutations.

According to the present invention, after transformation of host microorganisms with expression vectors containing the sequences coding for the said mutants and culturing the said organisms, polypeptides with improved IL-1ra activity are obtained and purified, replacing the residue in position 91 and/or the residue in position 109 in the sequence of extracellular IL-1ra or of other members of the IL-1ra family by the above mentioned amino acid.

Preferably, the residue in position 91 is replaced by an arginine residue and the residue in position 109 by an alanine residue. A particularly preferred mutant has an arginine residue in position 91 and an alanine residue in position 109.

Example 2 describes the preparation of the improved mutants of IL-1ra according to the invention, denoted for conciseness by the following symbols:

MILRA-1 N91→R

MILRA-2 T109→A

MILRA-3 N91/T109→R/A

These improved mutants possess an enhanced capacity for binding to the type I IL-1 receptor (IL-$1R_I$), together with an enhanced capacity for binding to the type II IL-1 receptor (IL-$1R_{II}$), so as to provide increased efficacy of inhibition even in pathological situations where IL-1ra functions little owing to the possible functional involvement of IL-$1R_{II}$ (neutrophilia, bone resorption, CNS effects, etc.).

To construct improved mutants of IL-1ra, the cDNA of IL-1ra was cloned in a suitable vector that would permit the appropriate genetic manipulations. The nucleotide sequence coding for IL-1ra is shown in Table 1 (Sequence ID No. 1), including the sequence that codes for the signal peptide of 25 amino acids. The amino acid sequence of IL-1ra is shown in Tables 1 and 2 (Sequence ID No. 2). Natural IL-1ra is expressed as a protein of 177 amino acids which, after removal of the signal sequence, gives rise to a mature molecule of 152 amino acids. The cDNA of IL-1ra is used for production of the IL-1ra protein, employing standard techniques. The gene can be inserted into an expression vector and the expression vector can be used for transforming a suitable host. The transformed host can be cultured in conditions that favour expression of the IL-1ra gene and, consequently, production of the IL-1ra protein.

These substitutions at positions 91 and/or 109 can be effected by site-specific mutagenesis using appropriate synthetic oligonucleotides. The recombinant gene is then inserted into the expression vector to produce the improved mutant.

For the therapeutic uses mentioned above, the mutated proteins of the invention will be administered in the form of pharmaceutical compositions suitable for parenteral, oral or topical administration, as described for example in "Remington's Pharmaceutical Sciences Handbook", Mack, Pub. Co., NY, USA, 17th ed. The average doses can vary from 2 μg/kg/h to 2 mg/kg/h by intravenous infusion, and from 2 μg/kg/day to 2 mg/kg/day by other administration routes.

EXAMPLE 1a

Cloning of the IL-1ra gene in *E. coli*

The CDNA coding for the IL-1ra protein is for example isolated by PCR from a cDNA pool prepared by conventional techniques from cells of monocytemacrophage origin. The oligonucleotides that can be used for selective amplification of the cDNA coding for IL-1ra are shown:

```
IL-1ra forward:  5'--GATCATATGCGACCCTCTGGGAGAAAATCC--3' (Sequence ID No. 3)
                    NdeI

IL-1ra reverse:  5'--GATCTGCAGCTACTCGTCCTCCTGGAAG--3'   (Sequence ID No. 4)
                    PstI
```

The forward oligonucleotide is designed so as to insert the NdeI restriction site immediately upstream from the codon encoding the first amino acid of the mature form of the protein (R26). The NdeI site permits insertion of a non-natural methionine which will constitute the initial amino acid of the recombinant proteins in question. Similarly, by means of the reverse oligonucleotide, a PstI restriction site is inserted immediately downstream from the stop codon of the protein. The amplified fragment is cloned at the NdeI and PstI sites of the expression vector pRSETA, obtaining the plasmid pRSETA-IL1ra. The map of the plasmid pRSETA-IL1ra is shown in FIG. 1.

EXAMPLE 1b

Clonina of the IL-1ra gene in *B. subtilis*

The cDNA coding for the IL-1ra protein is for example isolated by PCR from a cDNA pool, prepared by conventional techniques from cells of monocytemacrophage origin. The oligonucleotides that can be used for selective amplification of the cDNA encoding IL-1ra are shown:

```
IL-1ra forward:
5'-GGGAATTCTTATGCGACCCTCTGGGAGAAAATCC-3'           (Sequence ID No. 5)
     EcoRI

IL-1ra reverse:  5'--GGCTGCAGCTACTCGTCCTCCTGGAAG--3' (Sequence ID No. 6)
                      PstI
```

The forward oligonucleotide has been designed so as to insert the EcoRI restriction site immediately upstream from the codon encoding the amino acid methionine (indispensable for directing the start of translation of mRNA), followed by the codon encoding the first amino acid of the mature form of the protein (R26).

Similarly, by means of the reverse oligonucleotide, a PstI restriction site is inserted immediately downstream from the stop codon of the protein.

Figure 2:
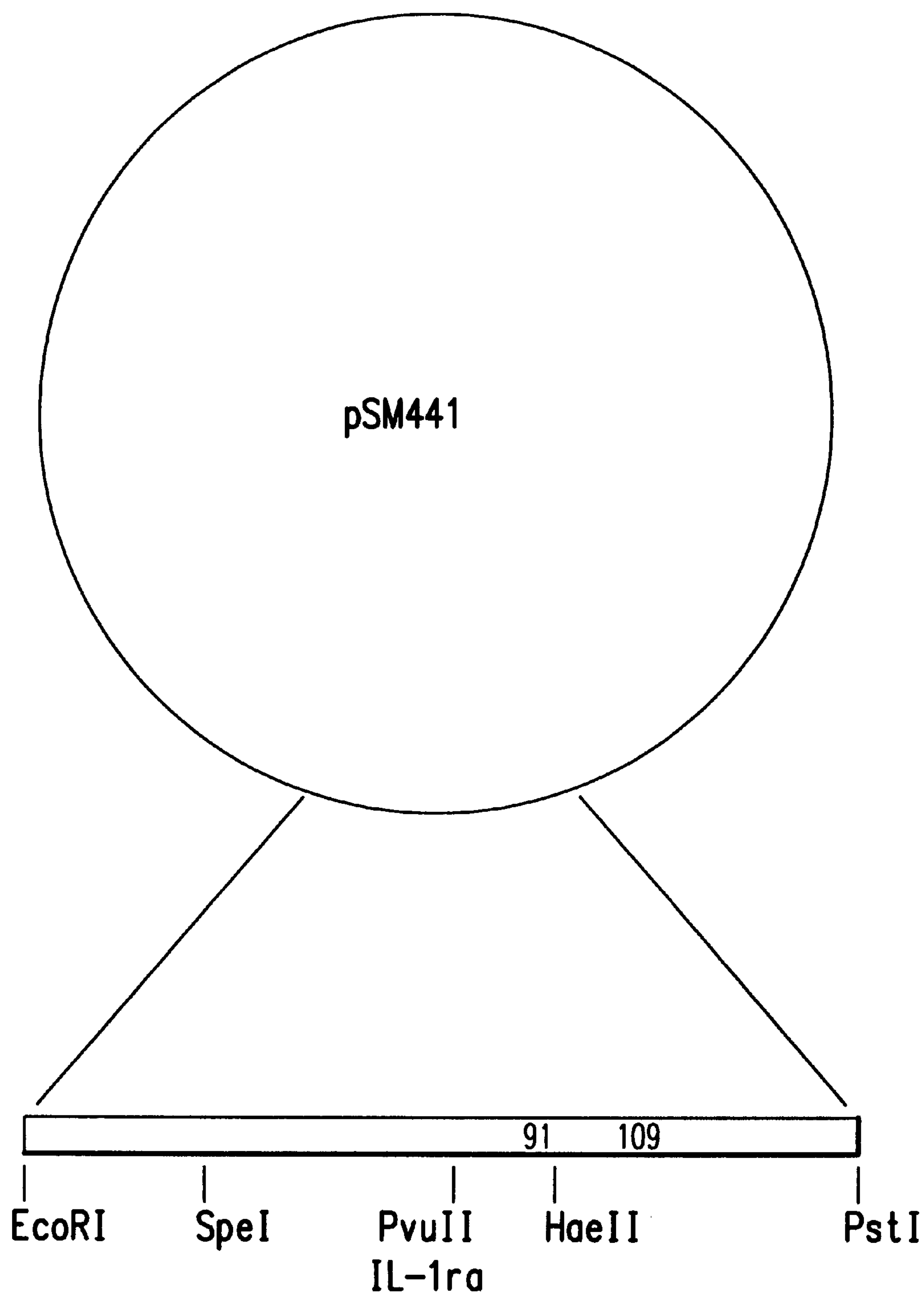
FIG. 2 shows a map of expression plasmid pSM441.

The amplified fragment is cloned at the EcoRI and PstI sites of the expression vector pSM671, obtaining the plasmid pSM441. The map of plasmid pSM441 is shown in FIG. 2.

EXAMPLE 2

Mutations of the IL-1ra gene

To obtain the desired mutations, part of the sequence coding for IL-1ra (amino acids 30–152) is transferred by cloning from plasmid pSM441 into the mutagenesis plasmid Bluescript SK$^+$ between the SpeI and PstI restriction sites, obtaining the plasmid BSK-IL1ra. Mutagenesis is effected using synthetic oligonucleotides, obtained with an Applied Biosystems 392 oligonucleotide synthesizer and utilizing phosphoramidite chemistry.

To obtain mutagenesis at site 91 of IL-1ra, the following complementary oligonucleotide, which is the reverse of the coding sequence, was used (Sequence ID No. 7):

```
1. 5' GTC CTG CTT TCT GCG CTC GCT CAG 3'
                      91
```

Sequence 1 can be modified on the anticodon corresponding to amino acid 91 so as to code for the other amino acids in that position.

To obtain the plasmid BSK-MILRA-1 (containing the mutation in position 91), the synthetic oligonucleotide is mixed with the single strand of DNA from the plasmid BSK-IL-1ra in a pairing buffer (5 pmol of oligonucleotide with 0.2 pmol of single strand in 10 ml of buffer), the mixture is heated to 70° C., then cooled slowly to 30° C. in 40 min and finally placed in ice. 1 ml of synthesis buffer, 1 ml (3 units) of T4 bNA ligase and 1 ml (0.5 unit) of T7 DNA polymerase are added to the mixture. After incubation for 1 hour at 37° C., the mixture is used to transform the competent cells. Identification of the positive clones is carried out by DNA sequencing.

Similarly, to obtain the plasmid BSK-MILRA-2, containing the T109→A mutation, the following oligonucleotide is synthesized (Sequence ID No. 8):

```
2. 5' CTC AAA ACT GGC GGT GGG GCC 3'
                 109
```

Alternatively, it is possible to use suitable oligonucleotides that code for the other amino acids in position 109. Then the same procedure is followed as for the N91→R mutation.

EXAMPLE 3

Insertion of the modified IL-1ra genes into expression vectors

The mutated sequence in plasmid BSK-MILRA-1 or BSK-MILRA-2 (mutation in position 91 or 109) is cut with SpeI and PstI and cloned directly into the expression plasmid pRSETA-IL1ra, between the same restriction sites, obtaining the expression plasmids pT7MILRA-1 and pT7MILRA-2. Cloning of the mutated sequences into the expression vector pSM441 was accomplished similarly, obtaining the expression plasmids pSM539 and pSM540. The sequence of the double mutant N91→R and T109→A is obtained by cloning between the SpeI and PstI sites of the vector pRSETA-IL1ra or of the vector pSM441, the SpeI-HaeII fragment of the BSK-MILRA-1 clone (amino acids 30–96) and HaeII-PstI fragment of the BSK-MILRA-2 clone (amino acids 97–152), obtaining the clone pT7MILRA-3 and pSMILRA-3 respectively.

EXAMPLE 4

Expression of the modified genes of IL-1ra

The expression plasmids pT7MILRA-1, pT7MILRA-2 and pT7MILRA-3 are transferred independently into cells of *E. coli* strain BL21 (DE3), which possess the gene for T7 RNA polymerase and so are capable of transcribing coding sequences downstream from plasmid T7. The cells are grown in LB culture medium containing 100 mg/l of ampicillin until an $OD_{590nm}$ of 0.7 is reached. Expression is induced at this point with 0.4 mM IPTG for 3–4 hours. The cells containing the protein expressed are harvested by centrifugation and frozen at −80° C. until the time of purification.

The expression plasmids pSM539, pSM540 and pSMILRA3 are transferred independently to cells of *B. subtilis* strain SMS118. The cells are grown in LB culture medium containing 5 mg/l of chloramphenicol for 16 hours at 30–37° C. The cells containing the protein expressed are harvested by centrifugation and frozen at −80° C. until the moment of purification.

EXAMPLE 5

Purification of the modified proteins expressed

For the mutant proteins of IL-1ra with improved activity to be obtained in an essentially pure form, extraction from the bacteria and purification of the homogenate are undertaken, for example according to the procedures indicated below.

1. Extraction: The bacteria are thawed, resuspended 1:3 (wet weight:volume) in 25 mM MES pH 6.25, 1 mM EDTA (buffer A) and sonicated in melting ice for 5 min (*E. coli*) or 15 min (*B. subtilis*) at a power of 60–70 W at intervals of 30 s. The homogenate is centrifuged at 30 000×g at 4° C. (or is put through some other suitable operation, e.g. tangential filtration). Aliquots of the supernatant and sediment are analysed in SDS-PAGE. Alternatively, extraction from the bacteria can be effected by some other suitable method. Aliquots of the supernatant and of the sediment are analysed in SDS-PAGE.
2. Q-Sepharose FF: The supernatant is adjusted to pH 6.0–6.5 and to a conductivity of 3–5 mS/cm and batch-incubated for 3 hours at 4° C. with stirring, with 1 ml/g of cells (wet weight) of Q-Sepharose Fast Flow (or some other suitable stationary ion-exchange phase) equilibrated in buffer A. Alternatively, the treatment can be carried out in a column, with isocratic elution in buffer A. The unadsorbed matter is then collected by filtration on a porous diaphragm. The gel is washed for 20 min as above in 2 volumes of buffer A; the wash liquid is collected as above. Aliquots of the unadsorbed matter and of the wash liquid are analysed in SDS-PAGE. The mutant protein of IL-1ra is found in the unadsorbed matter and in the wash liquid.

Point 2 can be postponed and effected in a column with isocratic elution in buffer A instead of gel filtration as in point 5.
3. S-Sepharose FF: The unadsorbed matter and the wash liquid of the Q-Sepharose FF are combined, filtered on 0.45 mm and loaded onto a column of S-Sepharose Fast Flow (or some other suitable stationary ion-exchange phase) equilibrated in buffer A. The unadsorbed matter is collected and buffer A is passed through until the baseline ($A_{280}$) falls to zero. Then a linear gradient is applied from 0.05 to 0.5M NaCl in buffer A in 2 column volumes, collecting the fractions. Alternatively, the linear gradient can be replaced by a stepped gradient, with intervals of 0.1M NaCl. Aliquots of the unadsorbed matter, of the fractions from gradient elution and of the eluted peak are analysed in SDS-PAGE. The mutant IL-1ra protein is found in the central fractions of the first peak eluted between 0.2 and 0.4M NaCl. Passage through Q-Sepharose FF and through S-Sepharose FF, as in points 2 and 3, can be reversed.
4. Filtration: The eluted peak of IL-1ra is concentrated and dialysed on Millipore Centriprep 10 filters, until the NaCl concentration falls below 50 mM; high molecular weight contaminants are removed by filtration on Millipore Centricon 100 centrifuge filters. Aliquots from the various filtrates are analysed in SDS-PAGE. Depending on the volumes to be treated, the operations described can be performed with various systems, using the same type of membrane.
5. Bio Gel P10: Any contaminants present, whether of higher or lower molecular weight, are removed by gel filtration in a column of Bio Gel P10 from Bio-Rad (or some other equivalent stationary phase for gel filtration) equilibrated and eluted in buffer A. Aliquots of the fractions eluted are analysed in SDS-PAGE. The mutant IL-1ra protein is found in the middle fractions of the first peak eluted after the excluded volume peak, in essentially pure form.

EXAMPLE 6

Characterization of inhibitory activity with the assay of binding to IL-1$R_I$ and IL-1$R_{II}$ The inhibitory activity of the improved IL-1ra mutants is measured in receptor binding assays, using IL-1ra as the reference standard. Cells which express IL-1$R_I$ selectively (e.g. the murine thymoma clone EL4-6.1) and cells which express IL-1$R_{II}$ selectively (e.g. Burkitt's human lymphoma RAJI clone 1H7) are chosen as target cells. The number of receptors per cell and the binding affinity (Kd) in both the lines are calculated from saturation curves obtained by incubating the cells ($10^6$ cells/test tube in a final volume of 0.1 ml of culture medium with $NaN_3$) with increasing doses of IL-1β labelled with $125_I$ in the presence or absence of a 500-fold molar excess of unlabelled IL-1β (for calculating non-specific binding, generally always less than 5–10%) for the optimum times and at the optimum temperatures for attaining equilibrium (generally 2 hours at room temperature) (Scapigliati et al. FEBS Lett. 243: 394, 1989). To calculate the inhibition activity, tests are conducted by incubating the cells with a concentration of radiolabelled IL-1β corresponding to approximately half of the Kd in the absence or in the presence of stepped doses of IL-1ra (reference standard) or of the improved mutant.

The improved inhibitory activity of the mutants is determined by calculating the shift of the inhibition curve towards the lower doses when compared with the curve of IL-1ra. An example of the results obtained (for MILRA-1 MILRA 2, and MILRA 3) is given in Table 3.

EXAMPLE 7

Characterization of antagonist activity with in-vitro assays of inhibition of IL-1β

The antagonist activity of the improved mutants of IL-1ra is evaluated by means of in-vitro biological assays of IL-1 activity. Two assays of this kind are described below.

1. Proliferation of murine thymocytes: normal thymocytes are obtained by breaking up thymus glands of C3H/HeJ mice (resistant to bacterial endotoxin) aged 4–8 weeks. The thymocytes ($5\times10^5$ cells/well of $Cluster^{96}$ plates) are incubated for 72 hours in RPMI-1640 culture medium with addition of antibiotics, L-glutamine, 2-ME, HEPES and 5% foetal calf serum at 37° C. in air with 5% $CO_2$. Incubation takes place in the presence of a suboptimal dose of the mitogen PHA (1.5 mg/ml, which does not induce significant proliferation of thymocytes) and stepped concentrations of IL-1β. To determine the proliferation of the thymocytes induced by IL-1, at the end of 72 hours of incubation 25 ml of culture medium containing 0.5 mCi of tritiated thymidine are added to each well. After another 18 hours, the cells from each well are harvested onto small glass-fibre disks and the radioactivity incorporated (proportional to the proliferation of the cells) is measured with a β-counter. For determination of the inhibitory capacity of the improved mutants of IL-1ra , the proliferation of the thymocytes is measured in response to the minimum dose of IL-1 that induces optimum proliferation (generally around 0.3 ng/ml) in the absence or in the presence of stepped doses of IL-1ra (control standard) or of the improved mutants. The improved inhibitory activity of the mutants is determined by calculating the shift of the inhibition curve towards the lower doses when compared with the curve of IL-1ra . An example of the results obtained (for MILRA-1) is presented in Table 3.
2. Induction of IL-6: cells of the continuous line of human osteosarcoma MG-63 are incubated ($5\times10^4$ cells/well of $Cluster^{96}$) for 48 hours in RPMI-1640 culture medium with antibiotics, L-glutamine, HEPES and 5% foetal calf serum in the absence or in the presence of stepped doses of IL-1β.

The quantity of IL-6 in the culture supernatants is measured by a commercial ELISA assay or determined in the biological assay of proliferation of 7TD1 cells. For evaluation of the antagonist capacity of the improved mutants of IL-1ra , the production of IL-6 is measured in MG-63 cells stimulated with the minimum dose of IL-1 capable of optimum induction of IL-6 (around 0.3 ng/ml) in the absence or in the presence of stepped doses of IL-1ra (control standard) or of the improved mutants of IL-1ra. The improved inhibitory activity of the mutants is determined by calculating the shift of the inhibition curve towards the lower doses when compared with the curve of IL-1ra .

An example of the results obtained (for MILRA-1 MILRA 2, anb MILRA-3) is presented in Table 3.

EXAMPLE 8

Characterization of antagonist activity by in-vivo assays of inhibition of IL-1β

The inhibitory activity of the improved mutants of IL-1ra is evaluated using in-vivo biological assays of IL-1 activity. Two assays of this kind are described below.

1. Induction of hypoglycaemia: C3H/HeJ mice or mice of some other strain (3–5 mice/test group) receive stepped doses of IL-1β by intraperitoneal administration. After two hours the animals are killed and the blood is collected for preparation of the serum. The serum glucose content is determined after reaction with glucose oxidase in a commercial calorimetric assay. To evaluate the antagonist capacity of the improved mutants of IL-1ra , induction of hypoglycaemia in vivo is effected by administering the minimum dose of IL-1β capable of inducing the optimum effect (generally around 5 mg/kg) in the absence or in the presence of stepped doses of IL-1ra (control standard) or of the improved mutants of IL-1ra.

The improved inhibitory activity of the mutants is determined by calculating the shift of the inhibition curve towards the lower doses when compared with the curve of IL-1ra . An example of the results obtained (for MILRA-1a) is presented in Table 3.

2. Induction of neutrophilia: C3H/HeJ mice or mice of some other strain (3 mice/test group) receive stepped doses of IL-1β with a single intraperitoneal administration. The increase of circulating neutrophils induced by IL-1 is evaluated by cytofluorimetry four hours after the treatment. The antagonist capacity of the improved mutants of IL-1ra is evaluated as inhibition of the neutrophilia induced by the minimum dose of IL-1 necessary to obtain the optimum increase of circulating neutrophils (generally around 150 ng/kg). IL-1ra (control standard) and the improved mutants are administered intraperitoneally on three occasions, at times −15 min, 0, +15 min, relative to IL-1β. The improved inhibitory activity of the mutants is determined by calculating the shift of the curve of inhibition towards the lower doses when compared with the curve of IL-1ra.

An example of the results obtained (for MILRA-1 MILRA-2, and MILRA-3) is presented in Table 3.

TABLE 1

NUCLEOTIDE AND AMINO ACID SEQUENCE OF IL-1ra

| | | |
|---|---|---|
| 1 | ATGGAAATCTGCAGAGGCCTCCGCAGTCACCTAATCACTCTCCTCCTCTTCCTGTTCCAT | |
| 1 | M E I C R G L R S H L I T L L L F L F H | |
| 61 | TCAGAGACGATCTGCCGACCCTCTGGGAGAAAATCCAGCAAGATGCAAGCCTTCAGAATC | |
| 21 | S E T I C R P S G R K S S K M Q A F R I | |
| 121 | TGGGATGTTAACCAGAAGACCTTCTATCTGAGGAACAACCAACTAGTTGCTGGATACTTG | |
| 41 | W D V N Q K T F Y L R N N Q L V A G Y L | |
| 181 | CAAGGACCAAATGTCAATTTAGAAGAAAAGATAGATGTGGTACCCATTGAGCCTCATGCT | |
| 61 | Q G P N V N L E E K I D V V P I E P H A | |
| 241 | CTGTTCTTGGGAATCCATGGAGGGAAGATGTGCCTGTCCTGTGTCAAGTCTGGTGATGAG | |
| 81 | L F L G I H G G K M C L S C V K S G D E | |
| 301 | ACCAGACTCCAGCTGGAGGCAGTTAACATCACTGACCTGAGCGAGAACAGAAAGCAGGAC | |
| 101 | T R L Q L E A V N I T D L S E N R K Q D | |
| 361 | AAGCGCTTCGCCTTCATCCGCTCAGACAGTGGCCCCACCACCAGTTTTGAGTCTGCCGCC | |
| 121 | K R F A F I R S D S G P T T S F E S A A | |
| 421 | TGCCCCGGTTGGTTCCTCTGCACAGCGATGGAAGCTGACCAGCCCGTCAGCCTCACCAAT | |
| 141 | C P G W F L C T A M E A D Q P V S L T N | |
| 481 | ATGCCTGACGAAGGCGTCATGGTCACCAAATTCTACTTCCAGGAGGACGAG | 531 |
| 161 | M P D E G V M V T K F Y F Q E D E | 177 |

TABLE 2

AMINO ACID SEQUENCE OF IL-1ra

| | | | | | |
|---|---|---|---|---|---|
| | | | | | 5 |
| MEICR GLRSH | | LITLL LFLFH | | SEITC | RPSGR |
| 10 | 15 | 20 | 25 | 30 | 35 |
| KSSKM | QAFRI | WDVNQ | KTFYL | RNNQL | VAGYL |
| 40 | 45 | 50 | 55 | 60 | 65 |
| QGPNV | NLEEK | IDVVP | IEPHA | LFLGI | HGGKM |
| 70 | 75 | 80 | 85 | 90 | 95 |
| CLSCV | KSGDE | TRLQL | EAVNI | TDLSE | NRKQD |
| | | | | | R |
| 100 | 105 | 110 | 115 | 120 | 125 |
| KRFAF | IRSDS | GPTTS | FESAA | CPGWF | LCTAM |
| | | A | | | |
| 130 | 135 | 140 | 145 | 150 | 152 |
| EADQP | VSLTN | MPDEG | VMVTK | FYFQE | DE |

NOTES:

The amino acids in italics represent the signal peptide, which is removed in the mature protein.

The numbering refers to the mature protein, without the signal peptide.

The amino acids in bold represent the two positions where the substitutions were planned, with the preferred substitution shown below.

TABLE 3

BIOLOGICAL ACTIVITY OF MILRA-1, MILRA-2 AND MILRA-3

| BIOLOGICAL ASSAY OF IL-1β INHIBITION | IL-1ra | MILRA-1 | MILRA-2 | MILRA-3 |
|---|---|---|---|---|
| In vitro: | | | | |
| Binding to IL-$1R_I$* | 0.34 nM | 0.17 nM | 0.19 nM | 0.22 nM |
| Binding to IL-$1R_{II}$* | 19.60 nM | 13.20 nM | 1.80 nH | 70.70 nM |
| Thymocyte proliferation** | | | | |
| to IL-1β 300 pg/ml | 4.10 ng/ml | 1.78 ng/ml | 1.75 ng/ml | n.t. |
| to IL-1β 30 pg/ml | 813 pg/ml | n.t. | n.t. | 285 pg/ml |
| IL-6 production** | 3.60 ng/ml | 0.62 ng/ml | 1.12 ng/ml | n.t. |
| In vivo: | | | | |
| Hypoglycaemia*** | 968.0 μg/kg | 128.0 μg/kg | n.t. | 76.0 μg/kg |
| Neutrophilia**** | 225.0 μg/kg | <22.5 μg/kg | n.t. | n.t. |

*Displacement of $^{125}$I IL-1β equilibrium binding 80.4–0.6 Nm $^{125}$I IL-1β on $10^6$ cells).
**Murine thymocyte proliferation in response to 0.3 ng/ml of IL-1β.
***Hypoglycaemia induced by in the mouse by 5.0 μg/kg IL-1β.
****Neutrophilia induced in the mouse by 150 ng/kg of IL-1β.
Doses reported are $ID_{50}$ except for neutrophilia, where $ID_{100}$ is indicated.
n.t. not tested

We claim:

1. A mutant of IL-1ra in which at least one of the amino acid residues in positions 91 and 109 of the sequence of wild type IL-1ra is replaced by a residue selected from the group consisting of glutamine, arginine, lysine, histidine, and tyrosine for position 91 and by a residue selected from the group consisting of serine, alanine, phenylalanine, valine, leucine, isoleucine, and methionine for position 109.

2. The mutant of IL-1ra according to claim 1, in which at least one of the amino acid residues in positions 91 and 109 of the sequence of wild type IL-1ra is replaced by a residue selected from the group consisting of arginine, lysine, histidine, and tyrosine for position 91 and by a residue selected from the group consisting of alanine, phenylalanine, valine, leucine, isoleucine, and methionine for position 109.

3. The mutant of IL-1ra according to claim 1, in which the amino acid residue in position 91 of the sequence of wild type IL-1ra is replaced by arginine.

4. The mutant of IL-1ra according to claim 1, in which the amino acid residue in position 109 of the sequence wild type Il-1ra is replaced by alanine.

5. The mutant of IL-1ra according to claim 1, in which both of the amino acid residues in positions 91 and 109 of the sequence of wild type IL-1ra are replaced respectively by arginine and alanine.

6. The mutant of IL-1ra according to claim 1, in which the sequence of IL-1ra is the sequence of an extracellular or intracellular IL-1ra.

7. A DNA sequence coding for the mutant of IL-1ra of claim 1.

8. The DNA sequence coding for the mutant of IL-1ra according to claim 7, further comprising regulating elements that permit their insertion into expression vectors.

9. An expression vector containing a DNA sequence of claim 7.

10. The expression vector of claim 9, being a plasmid selected from the group consisting of pT7MILRA-1, pT7MILRA-2, pSM539, pSM540, pT7MILRA-3, and pSMILRA-3.

11. A host cell transformed with the expression vector as in claim 9.

12. The host cell of claim 11, being a cell selected from the group consisting of *E. coli* strain BL21 and *B. subtilis* strain SMS118.

13. A method for the production, in essentially pure form, of the mutant of IL-1ra of claim 1 which comprises culturing in a culture medium host cells having expression vectors containing a nucleotide sequence for the mutant and recovering an expression product from the host cells or from the culture medium.

14. A pharmaceutical composition containing as active principle a mutant of IL-1ra as in claim 1 mixed with a suitable vehicle.

15. A method for inhibiting binding to IL-1$R_I$ receptors in cells which comprises treating said cells with the mutant of IL-1ra of claim 1.

16. A method for inhibiting proliferation of thymocytes which comprises treating cells with the mutant of IL-1ra of claim 1.

17. A method for antagonizing the production of IL-6 which comprises treating cells with the mutant IL-1ra of claim 1.

* * * * *